United States Patent [19]

Thompson

[11] 4,195,022

[45] Mar. 25, 1980

[54] 4-DESACETOXY-4α-HYDROXYVINBLASTINE AND RELATED COMPOUNDS

[75] Inventor: Gerald L. Thompson, Indianapolis, Ind.

[73] Assignee: Eli Lilly and Company, Indianapolis, Ind.

[21] Appl. No.: 890,422

[22] Filed: Mar. 27, 1978

[51] Int. Cl.² ........................................... C07D 519/04
[52] U.S. Cl. .................................. 260/244.4; 424/258
[58] Field of Search ........................ 260/287 B, 244.4; 424/258, 262

[56] References Cited

U.S. PATENT DOCUMENTS 3,392,173   7/1968   Hargrove ..................... 260/287 B

FOREIGN PATENT DOCUMENTS 2558027   7/1976   Fed. Rep. of Germany .
2558124   7/1976   Fed. Rep. of Germany .

*Primary Examiner*—David Wheeler
*Attorney, Agent, or Firm*—James L. Rowe; Arthur R. Whale

[57] ABSTRACT

4-Desacetoxy-4α-hydroxyvinblastine, prepared by reduction of 4-desacetoxy-4-oxovinblastine, and derivatives thereof, useful as antimitotic agents.

6 Claims, No Drawings

4-DESACETOXY-4α-HYDROXYVINBLASTINE AND RELATED COMPOUNDS

BACKGROUND OF THE INVENTION

The Vinca alkaloids, a group of dimeric indoledihydroindoles, have achieved considerable prominence as marketed or experimental chemotherapeutic drugs for the treatment of susceptible carcinomas, sarcomas, and leukemias. These agents are used both alone and in combination with other oncolytic agents. As a class, the Vinca alkaloids include compounds obtainable from the leaves of *Vinca rosea*, derivatives produced by chemical modification thereof and more recently, dimeric alkaloids produced by coupling two "monomeric" indoles via a modified Polonovski reaction-see Langlois and Potier, *Tetrahedron Letters*, 1099 (1976), Potier, et al., *J.C.S. Chem. Comm.*, 670 (1975), Kutney et al., *Heterocycles*, 3, 205 (1975) and Atta-ur-Rahman, *Tetrahedron Letters*, 2351 (1976).

A majority of the known Vinca alkaloids can be represented by the following formula:

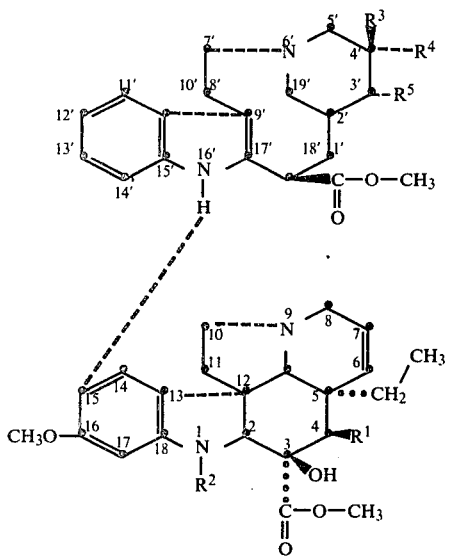

In the above formula, where $R^1$ is acetoxy, $R^2$ is methyl, $R^3$ is hydroxyl, $R^4$ is ethyl and $R^5$ is H, vinblastine is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hydroxyl and $R^5$ is H, leurosidine is represented; where $R^1$ is acetoxy, $R^2$ is methyl, $R^3$ and $R^5$ are H and $R^4$ is ethyl, deoxy VLB "A" is represented; where $R^1$, $R^2$ and $R^5$ are the same as in deoxy VLB "A" (4'-deoxyvinblastine) but $R^3$ is ethyl and $R^4$ is hydrogen, deoxy VLB "B" (4'-deoxyleurosidine) is represented; where $R^1$ is acetoxy, $R^2$ is methyl, $R^3$ is ethyl and $R^4$ and $R^5$ taken together form an α-epoxide ring, leurosine is represented; and where $R^1$, $R^3$, $R^4$ and $R^5$ are the same as in leurosine but $R^2$ is formyl, leuroformine (N-formylleurosine) is represented.

The above-mentioned alkaloids are described in the following publications: leurosine (vinleurosine—U.S. Pat. No. 3,370,057), VLB (vincaleukoblastine, vinblastine—U.S. Pat. No. 3,097,137), leurosidine (vinrosidine) and vincristine (leurocristine or VCR) (both in U.S. Pat. No. 3,205,220), and deoxy VLB "A" and "B", *Tetrahedron Letters*, 783 (1958). Other alkaloids obtainable from vinca rosea include 4-desacetoxy vinblastine (U.S. Pat. No. 3,954,773); 4-desacetoxy-3'-hydroxyvinblastine (U.S. Pat. No. 3,944,554); leurocolombine (2'-hydroxy VLB—U.S. Pat. No. 3,890,325) and vicadioline (3'-hydroxy VLB—U.S. Pat. No. 3,887,565).

Two of the above alkaloids, VLB and vincristine, are now marketed as drugs for the treatment of malignancies, particularly the leukemias and related diseases in humans. Of these marketed compounds, vincristine is a most active and useful agent in the treatment of leukemias but is also the least abundant of the antineoplastic alkaloids of *Vinca rosea*. Jovanovics et al.—U.S. Pat. No. 3,899,493—have developed an elegant oxidative procedure for converting the more abundant alkaloid VLB to vincristine employing chromic acid in acetone and acetic acid at about −60° C. The same procedure has been used to prepare leuroformine (N-formylleurosine) from leurosine—see Belgian patent No. 811,110. Leuroformine is currently undergoing a clinical trial in Europe, chiefly in treatment of the leukemias and of multiple myeloma.

Chemical modification of VLB and vincristine has included hydrolysis of the 4-acetoxy group to yield 4-desacetyl VLB (DAVLB) or 4-desacetylvincristine (DAVCR) followed by reesterification with other acyl and amino-acyl groups—see U.S. Pat. Nos. 3,392,173 and 3,387,001—, and replacement of the C-3 ester function by an amide function—see Belgian patent 837,390. One of the former 4-acyl derivatives, the 4-N,N-dimethylglycine ester underwent a brief clinical trial and one of the latter, vindesine, (4-desacetyl VLB C-3 carboxamide) is currently being tested clinically against a variety of neoplasms.

Other chemical modification of the VLB molecule such as hydrolysis and decarboxylation of the C-18' carbomethoxy group has resulted in a loss of anti-cancer activity as has the formation of N-oxides; i.e., pleurosine (leurosine N-oxide). Oxidative attack on VLB under reaction conditions different from those of Jovanovics (loc. cit.) has resulted in the formation of a chemotherapeutically-inactive compound, vinamidine, which alkaloid has also been encountered in alkaloidal fractions from *Vinca rosea* leaves—see Tafur et al. *J. Pharm. Sci.*, 64, 1953 (1975).

It is an object of this invention to prepare derivatives of oncolytically active Vinca alkaloids having either a different anti-tumor spectrum, or lessened or different side effects, or both as compared with the marketed drugs, vinblastine and vincristine.

SUMMARY OF THE INVENTION

In fulfillment of the above and other objects, this invention provides dimeric indole-dihydroindole alkaloids of the formula:

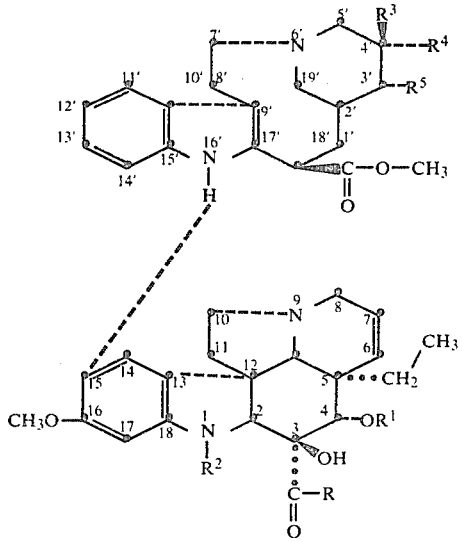

II

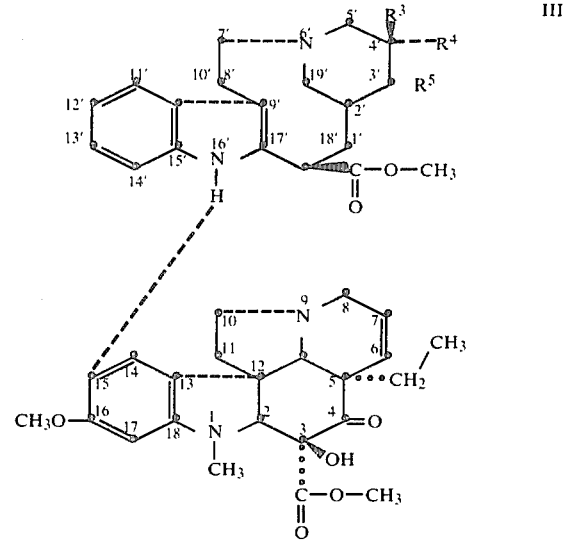

III wherein R is OCH₃ or NH-NH₂, $R^1$ is H or acetyl, $R^2$ is CH₃ or CHO, and, when taken singly, $R^5$ is H and one of $R^3$ and $R^4$ is OH or H and the other is C₂H₅ and when $R^4$ and $R^5$ are taken together they form an α-epoxide ring and $R^3$ is C₂H₅, with the proviso that, when R is NH-NH₂, $R^1$ is H.

The compounds of Formula II thus include, when $R^2$ is CH₃, 4-epi hydroxy or acetoxy (or alternatively, 4α-hydroxy or acetoxy) derivatives of vinblastine, leurosidine, leurosine, and deoxy VLB "A" and "B", all known oncolytic agents and when $R^2$ is CHO, derivatives of vincristine, 1-formylleurosine (leuroformine), 1-formylleurosidine, 4'-deoxy-1-formylleurosidine and 4'-deoxyvincristine, the latter two being disclosed in my copending application Ser. No. 760,595 filed Jan. 19, 1977.

Also included within the scope of this invention are the pharmaceutically-acceptable acid addition salts of the above alkaloidal bases including salts derived from inorganic acids such as: hydrochloric acid, nitric acid, phosphoric acid, sulfuric acid, hydrobromic acid, hydriodic acid, nitrous acid, phosphorus acid and the like, as well as salts of organic acids including aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include the sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, napthalene-2-sulfonate and the like salts.

The alkaloidal bases of this invention when $R^1$ is H, $R^2$ is CH₃ and R is OCH₃ are prepared by reducing a compound of the formula wherein $R^3$, $R^4$ and $R^5$ have the same meaning as hereinabove, with LiAlH(t-butyloxy)₃ in dry THF (tetrahydrofuran). An excess of reducing agent is customarily employed in this reaction. Other non-reactive anhydrous solvents such as diethylether can be employed in place of THF.

Compounds according to Formula II above in which $R^2$ is CHO and R is OCH₃ are prepared by low temperature chromic acid-acetic acid oxidation of the corresponding compound in which $R^2$ is methyl. The reaction conditions employed are in general those of Jovanovics (Loc. cit). Compounds in which R is NH—NH₂ and $R^2$ is CHO or CH₃ are prepared by reacting hydrazine hydrate with the corresponding compound in which R is methoxy, prepared by the procedures indicated above. Compounds in which $R^2$ is methyl or formyl and R is methoxy and $R^1$ is acetyl are prepared by acetylation of the corresponding compound in which $R^1$ is H. The following compounds illustrate the scope of this invention:

4-desacetoxy-4α-acetoxyleurosine
4-desacetoxy-4α-acetoxyvinblastine
4-desacetoxy-4α-acetoxyleuroformine
4'-deoxy-4-desacetoxy-4α-acetoxyleurosidine
4'-deoxy-4-desacetoxy-4α-hydroxyvinblastine
4'-deoxy-4-desacetoxy-4α-hydroxy-1-formylleurosidine
4-desacetoxy-4α-acetoxyvincristine
4-desacetoxy-4α-hydroxyleurosine
4'-deoxy-4-desacetoxy-4α-hydroxyvincristine This invention is further illustrated by the following specific examples.

EXAMPLE 1

Preparation of 4-Desacetoxy-4α-hydroxyvinblastine

A solution was prepared from 76.6 mg. of 4-desacetoxy-4-oxovinblastine prepared by the procedure of Wright and Neuss as disclosed in copending application Ser. No. 848,837 filed Nov. 7, 1977 and 0.90 ml. of anhydrous tetrahydrofuran (THF). All equipment used in forming the solution and carrying out the reaction was oven dried. 76.2 Milligrams of LiAlH(t-Buo)₃ were added to the above solution. The reaction mixture was stirred at room temperature in a sealed flask under nitrogen atmosphere for about 22 hours. Next, a solution of 0.11 g. of ammonium sulfate and 0.17 ml. of water were added. Infusorial earth was next added and the reaction mixture filtered through infusorial earth. The filter cake was washed with THF. The clear colorless filtrate was concentrated in vacuo and the resulting residue comprising 4-desacetoxy-4α-hydroxyvinblastine formed in the above reaction was dissolved in methylene dichloride. Removal of the methylene dichloride gave 78.7 mg. of a white solid which was shown by TLC to be chiefly one spot material. The residue was chromatographed over 20 g. of Woelm silica gel using 2:1 benzene/chloroform containing 6, 9, 13.5, 20, 30, and 45 percent methanol for each 30 ml. portion of eluant. Ten ml. fractions were taken. Fractions 7–12 were combined to give, after evaporation of the solvents, 55.1 mg. of a bright yellow solid shown to be essentially one-spot material on TLC. Recrystallization from ethanol yielded 28.8 mg. of fluffy white crystals. 4-Desacetoxy-4α-hydroxyvinblastine thus prepared has the following physical characteristics:

100 MHz pmr spectrum:

$\delta(COCl_3)$ 8.23 (br s 1, indole N—H), 7.43–7.61 (m, 1, $C_{11}$—H), 7.01–7.22 (m, 3, $C_{12',14'}$-H), 6.59 (s, 1, $C_{14}$—H), 6.05 (s, 1, $C_{17}$—H), 5.66–5.77 (m, 2, $C_{6,7}$—H), 4.02 (d, J=3, 1, $C_4$—H), 3.88 (s, 3, $C_{15}$—$OCH_3$), 3.75 (s, 3, $C_3$—$CO_2CH_3$), 3.73 (br, s 1, $C_2$—H), 3.59 (s, 3, $C_{18'}$—$CO_2CH_3$), 2.85 (s, 3, N—$CH_3$), 0.98 and 0.87 (2t, J=7, 6, $C_{21,21'}$—H).

Infra-red spectrum:

$\nu(CHCl_3)$=3465, 3005, 1724, 1616, 1500, 1458, 1432 cm$^{-1}$.

Ultra-violet spectrum:

$\lambda(EtOH)$=214 ($\epsilon 4.46 \times 10^4$), 288, 296 nm.

Mass spectrum:

m/e 768 (M+), 737, 709, 651, 543, 154.

EXAMPLE 2

Preparation of 4-Desacetoxy-4α-hydroxyvincristine

A solution was prepared from 76.8 mg. of 4-desacetoxy-4α-hydroxyvinblastine and 10 ml. of acetone. 43.5 μl. of an acidic solution prepared from 19.9 ml. of water and 2.5 ml. of 18 M sulfuric acid were added. A fine precipitate formed immediately. This acidic mixture was cooled to about −60° C. and an oxidizing solution containing 90 mg. of chromium trioxide in 1 ml. of glacial acetic acid and 0.1 ml. of water was added thereto in dropwise fashion over a 4-minute period. The reaction mixture was stirred in the range −60° to −50° C. for twenty minutes and then cooled to −70° C. Two milliliters of 14 N aqueous ammonium hydroxide were added and the resulting mixture poured into 50 ml. of an ice-water mixture. The aqueous layer was extracted three times with chloroform, and the chloroform extracts combined. The combined extracts were washed with dilute sodium bisulfite and then dried. Evaporation of the solvent yielded 61.6 mg. of a light yellow solid residue. The residue was chromatographed over 20 g. of Woelm activity I silica gel. The chromatogram was developed with 30 ml. portions of 1:1 methylenedichloride/ethyl acetate containing 4, 6, 9, 13.5, 20, and 30 percent methanol. Ten milliliter fractions were taken. Fractions 15 to 20 were combined to give 34.8 mg. of a white solid consisting of 4-desacetoxy-4α-hydroxyvincristine formed in the above reaction.

The residue was dissolved in anhydrous ethanol and 124 μl. of 2 percent v/v aqueous sulfuric acid in anhydrous ethanol was added, thus forming the sulfate salt of 4-desacetoxy-4α-hydroxyvinblastine. The free base had the following physical characteristics: Mass spectrum: m/e 782 (M+), 751, 355, 154.

EXAMPLE 3

Preparation of 4-Desacetoxy-4α-hydroxyvinblastine C-3 carboxhydrazide

A reaction mixture was prepared from 76.8 mg. of 4-desacetoxy-4α-hydroxyvinblastine, 6 ml. of anhydrous hydrazine (97 percent) and 9 ml. of anhydrous methanol. The reaction vessels were over dried and flushed with nitrogen. The reaction mixture was heated at 53° C. for 24 hours and was then concentrated in vacuo. The resulting residue was twice dissolved in methylene dichloride and the resulting methylene dichloride extract concentrated in vacuo to yield a white solid residue which showed one major spot on TLC and no spot corresponding to starting material. The white solid was chromatographed over 22 g. of Woelm activity I silica gel. The chromatogram was developed with 30 ml. portions of 2:1 benzene/chloroform containing 4, 6, 9, 13.5, 20, 30, and 45 percent methanol. Ten milliliter fractions were taken. Fractions 15–23 were combined to yield 54.3 mg. of 4-desacetoxy-4α-hydroxyvinblastine C-3 carboxhydrazide, having the following physical characteristics: Mass spectrum: m/e 768 (M+), 737, 709, 651, 154 Infra-red spectrum: $\nu(CHCl_3)$ 3430, 3050, 1720, 1655, 1615, 1497, 1455, 1428, 1220 cm$^{-1}$.

EXAMPLE 4

PREPARATION OF 4-EPI-VLB (4-DESACETOXY-4α-ACETOXY VLB)

A reaction mixture containing 440 mg. of 4-desacetoxy-4α-hydroxy VLB, 6 ml. of acetic anhydride and 6 ml. of pyridine, was prepared and allowed to remain at ambient temperature for 17 hours. Volatile constituents were removed in vacuo at 30° C. The residual oil comprising 4-epi VLB formed in the above acetylation, was dissolved in methylene chloride. The organic layer was washed with cold water. The aqueous layer was separated and extracted with methylene chloride. This methylene chloride extract was added to the original layer and the combined layers were dried. Evaporation of the solvent yielded a residue of 4-epi-VLB which was purified by chromatography over 20 g. of silica gel (Activity I), using 1:1 methylene chloride/ethyl acetate containing increasing amounts (9, 13.5, 30 and 45 percent) of methanol as the eluting solvent. Fractions shown to contain 4-epi-VLB by TLC were combined and the solvent removed from the combined extracts. The resulting residue was a yellow solid comprising 14-epi-VLB with the following physical characteristics:

100 MHz pmr spectrum:

$\delta(CDCl_3)$ 8.41 (br, s, 1, indole N—H), 7.39–7.58 (m, 1, $C_{11}$—H), 7.0–7.3 (m, 3, $C_{12',14'}$—H), 6.58 (s, 1, $C_{14}$—H), 6.03 (s, 1, $C_{17}$—H), 5.49–5.82 (m, 2, $C_{6,7}$—H), 4.56 (s, 1, $C_4$—H), 3.79 (s, 3, $C_{15}$—$OCH_3$), 3.75 (s, 3, $C_3$—$CO_2CH_3$), 3.60 (s, 3, $C_{18'}$—$CO_2CH_3$), 2.90 (s, 3, N—$CH_3$), 1.25 and 0.90 (2t, J=7, 6, $C_{21,21'}$—H).

Infra-red spectrum:

$\nu(CHCl_3) = 3450, 3000, 1730, 1225$ cm$^{-1}$.

Ultra-violet spectrum:

$\lambda(EtOAc) = 214$ ($\epsilon 4.46 \times 10^4$), 288, 296 nm.

Mass spectrum:

m/e 810 (M+), 779, 751, 469, 295, 154.

The sulfate salt was prepared in ethanolic sulfuric acid at pH=2.

Leurosidine, deoxy VLB "A", deoxy VLB "B" and leurosine can be subjected to the same series of reactions; i.e., mild alkaline hydrolysis to form the 4-desacetyl derivative, oxidation of the 4-hydroxy derivative to the 4-oxo derivative, reduction of the 4-oxo derivative with LiAlH(t-BuO)$_3$ to yield the corresponding 4-desacetoxy-4α-hydroxy derivative. Each of these derivatives can then be oxidized to yield the corresponding vincristine-type derivative (compounds wherein R$^2$ is CHO); then any of the compounds can be reacted with hydrazine to yield the corresponding C-3 carboxhydrazide.

Any of the 4α-hydroxy derivatives of this invention except those in which R is NH-NH$_2$ can be acetylated with acetic anhydride in the presence of base to yield a corresponding 4α-acetoxy derivative.

The compounds of this invention are mitotic inhibitors in Chinese hamster ovary cells. In particular, 4-desacetoxy-4α-hydroxyvinblastine shows a mitotic inhibition roughly corresponding to that seen with either vinblastine sulfate or with 4-desacetylvinblastine, manifesting an activity as low as 0.01 mcg/ml.

The compounds of this invention, as represented by Formula II above, are anti-tumor agents. They demonstrate this activity against transplanted tumors in mice. For this determination, a protocol was used which involved the administration of the drug by the intraperitoneal route at a given dose level for 7–10 days after innoculation with the tumor or alternatively, on the first, fifth, and ninth days after innoculation.

The following table—Table 1—give the results of several experiments in which transplanted tumors in mice were treated successfully with a compound of this invention.

In the table, column 1 gives the name of the compound; column 2, the transplanted tumor; column 3, the dose level or dose level range and the number of days the dosage was administered; and column 4, the percent inhibition of tumor growth or percent prolongation of survival time, e.g., B16. (GLS is an abbreviation for Gardner lymphosarcoma; CA755 is an adenocarcinoma; and B16 is a melanoma.).

| Compound | Tumor | mg./kg. × Days | Percent Inhibition or Prolongation of Survival Time |
|---|---|---|---|
| 4-Desacetoxy-4α-hydroxy-vinblastine | GLS | 6.0 × 10 | 100 (day 7) toxic |
| | | 3.0 × 10 | 91 (day 7) 78 (day 11) |
| | | 1.5 × 10 | 35 (day 7) 25 (day 11) |
| | B16 | 9.0 × 3 | toxic |
| | | 6.0 × 3 | 90 |
| | | 3.0 × 3 | 65 |
| | 755 | 3.0 × 10 | 38 |
| 4-Desacetoxy-4α-hydroxy-vincristine sulfate | GLS | 6.0 × 10 | 100 (day 7) toxic |
| | | 3.0 × 10 | 100 (day 7) 100 (day 11) |
| | | 1.5 × 10 | 36 (day 7) 29 (day 11) |
| 4-Desacetoxy-4α-hydroxy-vinblastine C-3 carbox-hydrazide | GLS | 6.0 × 10 | toxic |
| | | 3.0 × 10 | 100 (day 7) 100 (day 11) |
| | | 1.5 × 10 | 97 (day 7) 98 (day 11) |
| | B16 | 9.0 × 3 | toxic |
| | | 6.0 × 3 | 121* |
| | | 3.0 × 3 | 67 |

*Indefinite Survivors

In utilizing the novel compounds of this invention an anti-tumor agents, either the parenteral or oral route of administration may be employed. For oral dosage, a suitable quantity of a pharmaceutically-acceptable salt of a base according to Formula II formed with a non-toxic acid, such as the sulfate salt, is mixed with starch or other excipient and the mixture placed in telescoping gelatin capsules each containing from 7.5 to 50 mg. of active ingredients. Similarly, the anti-neoplastically active salt can be mixed with starch, a binder and a lubricant and the mixture compressed into tablets each containing from the 7.5–50 mgs. of salt. The tablets may be scored if lower or divided dosages are to be used. Parenteral administration is preferred however. For this purpose, isotonic solutions are employed containing 1–10 mg./ml. of a salt of an indoledihydroindole of Formula II such as the sulfate salt. The compounds are administered at the rate of from 0.01 to 1 mg/kg. and preferably from 0.1 to 1 mg./kg. of mammalian body weight once or twice a week or every two weeks depending on both the activity and the toxicity of the drug. An alternative method of arriving at a therapeutic dose is based on body-surface area with a dose in the range 0.1 to 10 mg./meter squared of mammalian body surface every 7 or 14 days being administered.

In utilizing a compound of this invention clinically, the clinical physician would administer the compound initially by the same route and in the same vehicle and probably against the same types of tumors as are indicated for vincristine or VLB. The dose levels employed would reflect the difference in dose levels found in the treatment of experimental tumors in mice, the dose levels of the compounds of this invention being less than those used with vincristine and VLB. In clinical tests, as with other anti-tumor agents, particular attention would be paid to the effect of the oncolytic compounds of this invention against the ten "signal" tumors set forth at page 266 of "The Design of Clinical Trials in Cancer Therapy" edited by Staquet (Futura Publishing Company, 1973)

We claim:

1. An indole-dihydroindole of the formula

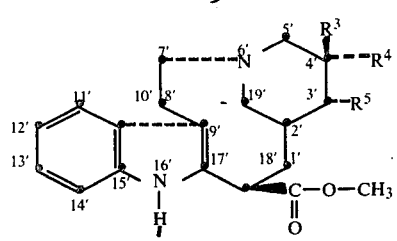

wherein R is $OCH_3$ or $NH-NH_2$, $R^1$ is H or acetyl, $R^2$ is $CH_3$ or CHO, and, when taken singly, $R^5$ is H and one of $R^3$ and $R^4$ is OH or H and the other is $C_2H_5$ and when $R^4$ and $R^5$ are taken together, they form an α-epoxide ring and $R^3$ is $C_2H_5$, with the proviso that, when R is $NH-NH_2$, $R^1$ is H, and pharmaceutically acceptable acid addition salts thereof.

2. A compound according to claim 1 in which R is $OCH_3$, $R^1$ is H, $R^2$ is $CH_3$, $R^3$ is OH, $R^4$ is $C_2H_5$ and $R^5$ is H, said compound being 4-desacetoxy-4α-hydroxyvinblastine.

3. A compound according to claim 1 in which R is $OCH_3$, $R^1$ is H, $R^2$ is CHO, $R^3$ is OH, $R^4$ is $C_2H_5$ and $R^5$ is H, said compound being 4-desacetoxy-4α-hydroxyvincristine.

4. The sulfate salt of the compound of claim 3.

5. A compound according to claim 1 in which R is $NH-NH_2$, $R^1$ is H, $R^2$ is $CH_3$, $R^3$ is OH, $R^4$ is $C_2H_5$ and $R^5$ is H, said compound being 4-desacetoxy-4α-hydroxyvinblastine C-3 carboxhydrazide.

6. A sulfate salt of a compound according to claim 1.

* * * * *